United States Patent
Völkl et al.

(10) Patent No.: US 7,922,489 B2
(45) Date of Patent: Apr. 12, 2011

(54) PROCEDURE FOR DETERMINING THE FORM OF A RESIDUAL TOOTH AREA

(75) Inventors: Lothar Völkl, Goldbach (DE); Philip Von Schroeter, Rodenbach (DE)

(73) Assignee: Degudent GmbH, Hanau (DE)

( * ) Notice: Subject to any disclaimer, the term of this patent is extended or adjusted under 35 U.S.C. 154(b) by 0 days.

(21) Appl. No.: 10/576,510

(22) PCT Filed: Dec. 8, 2004

(86) PCT No.: PCT/EP2004/013964
§ 371 (c)(1),
(2), (4) Date: May 24, 2006

(87) PCT Pub. No.: WO2005/058183
PCT Pub. Date: Jun. 30, 2005

(65) Prior Publication Data
US 2007/0072151 A1 Mar. 29, 2007

(30) Foreign Application Priority Data
Dec. 9, 2003 (DE) .................................. 103 57 699

(51) Int. Cl.
*A61C 11/00* (2006.01)
*A61C 5/10* (2006.01)
(52) U.S. Cl. ........................................ 433/213; 433/223
(58) Field of Classification Search .................. 433/213, 433/218, 223, 215; 382/129, 135, 170, 171, 382/173, 175, 284, 294, 315
See application file for complete search history.

(56) References Cited

U.S. PATENT DOCUMENTS

| | | | |
|---|---|---|---|
| 4,767,330 A | 8/1988 | Burger et al. | |
| 5,338,198 A | 8/1994 | Wu et al. | |
| 5,605,459 A | 2/1997 | Kuroda et al. | |
| 5,607,305 A * | 3/1997 | Andersson et al. | 433/213 |
| 5,644,411 A * | 7/1997 | Tamagaki et al. | 358/529 |
| 6,287,121 B1 | 9/2001 | Guiot et al. | |
| 2003/0124492 A1 | 7/2003 | Perot | |

FOREIGN PATENT DOCUMENTS

| | | |
|---|---|---|
| DE | 29 920236 | 4/2000 |
| DE | 29 110518 | 7/2002 |
| EP | 0 913130 | 5/1999 |
| EP | 0 731673 | 5/2001 |

* cited by examiner

*Primary Examiner* — Cris L Rodriguez
*Assistant Examiner* — Heidi M Eide
(74) *Attorney, Agent, or Firm* — Dennison, Schultz & MacDonald

(57) ABSTRACT

The invention relates to a process for determining the form a duplicate of a residual tooth area, which is to be fitted with a dental restoration whereby the duplicate sections to be fitted with the restoration are removed from the duplicate and the form data to be allocated to their forms has to be determined and stored in a computer, by means of which the form of the restoration is calculated taking into consideration the spatial allocation of the duplicate sections. In order to be able to determine the shape of the residual tooth area to be fitted with the restoration, and thereby determine the shape of the restoration itself with high precision, it is proposed that the duplicate sections are or are being individually referenced to each other in their spatial allocation to each other according to a referencing stored in the computer.

14 Claims, 2 Drawing Sheets

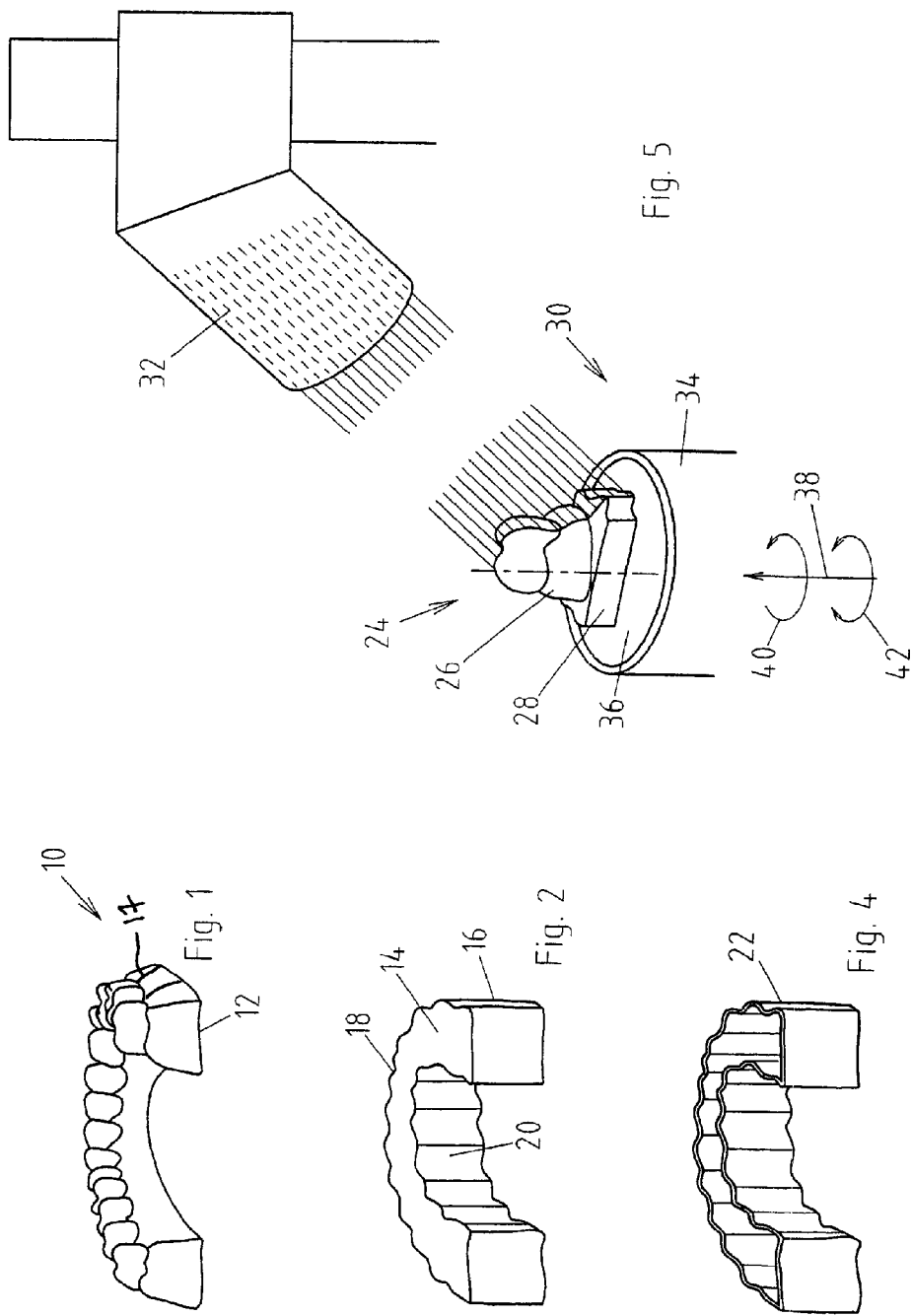

PROCEDURE FOR DETERMINING THE FORM OF A RESIDUAL TOOTH AREA

Figure 3:
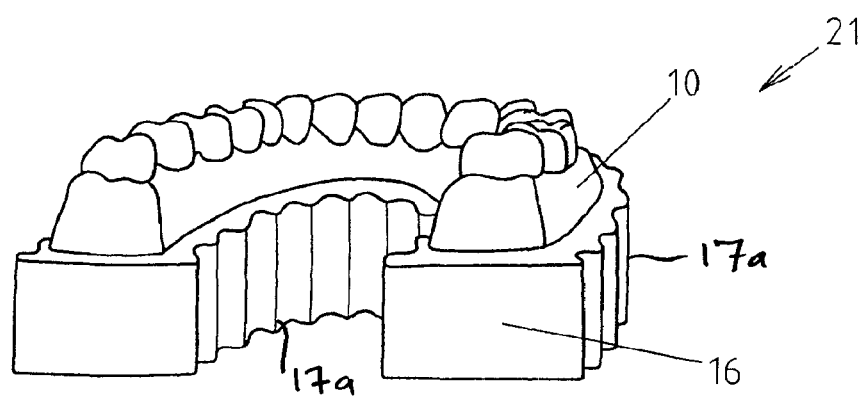

This application is a filing under 35 USC 371 of PCT/EP2004/013964, filed Dec. 8, 2004.

The invention relates to a process for determining the form of a duplicate of a residual tooth area, which is to be fitted with a dental restoration such as a bridge or framework, whereby the duplicate sections to be fitted with the restoration and/or duplicate sections determining their design are taken from the duplicate, and the form data to be allocated to their forms has to be determined and stored in a computer, by means of which the form of the restoration is calculated taking into consideration the spatial allocation of the duplicate sections.

A corresponding process can be taken from EP 0 731 673 B1 (WO 96/10371). It is thereby provided, that in a first procedural step reciprocal positions of the duplicate sections are determined in the duplicate by means of a leveling apparatus. In a second step the duplicate sections taken out from the duplicate are scanned by means of a scanning unit to determine contour data.

Finally, in the third step, the contour data are linked with the position data.

Such a process involves great expense due to the required hardware and consequently bears numerous sources of errors.

From EP-B-0 913 130, a process for producing a dental prosthesis is known, in which the form of a duplicate is determined, then the duplicate is split apart, forms of the removed duplicate sections are determined, and finally the data of the duplicate and of the duplicate sections are combined. Such a process results in exact measurements; however, besides expensive software, it requires expensive technical means to scan the duplicate and the duplicate sections. The special clamping devices that are required also must be aligned with a scanner.

The present invention is based on the need for a process of the above mentioned type so that the form of the residual tooth area to be fitted with the restoration, or the design determining the restoration and therefore the form of the restoration itself, can be determined with a high degree of accuracy. At the same time instrument-related measuring errors can be minimized.

To solve this problem the invention essentially provides that the removed duplicate sections are individually referenced to each other according to a reference system stored in the computer and which is dependent on the duplicate, and that these data are linked for determining the form of the dental restoration in the computer with the form data of the duplicate sections. In other words, the invention provides that the duplicate sections are or are being referenced individually to each other in their spatial allocation according to a reference system stored in the computer.

Referencing independently from the duplicate means, not that the geometry of the duplicate which is obtained by the individual casting of the residual tooth or jaw area to be fitted with the dental prosthesis and according to EP-B-0 913 130 is imperatively used for referencing per se, but that a referencing determined or predetermined independently from the individual geometry of the duplicate, which is stored in the computer, is used to allocate the duplicate sections to each other spatially and geometrically. This, however, does not preclude that already during the fabrication of the duplicate or during casting taking by using (e.g.) a referencing impression spoon, a desired referencing is embossed independently of the individual course of the duplicate of the residual tooth or jaw area.

In deviation from the prior known state of the art, it is no longer necessary to completely scan the duplicate or to use a leveling apparatus to determine the position of the duplicate sections to each other, which are to be fitted with the dental restoration. Instead it is only necessary to reference the duplicate thereupon, in consideration of this referencing, to determine the form of the duplicate sections by e.g. scanning, whereby the referencing presets the spatial allocation of the duplicate sections; that is the spatial reference is determined from the referencing.

The referencing does not occur via the duplicate itself, as this is the case in the state of the art. Rather the duplicate is preferably aligned to a seat such as a holding device, particularly a base plate holding the duplicate, which in turn is referenced. Thus an existing referencing is utilized, which ensures an unequivocal geometric relationship between the duplicate sections.

Data corresponding to the referencing are stored in the computer so that the only new data to be entered is that corresponding to the form of the duplicate sections. Thus a simplification of the software takes place. There are also benefits with respect to the apparatus in that there is only one holding device or one type of holding device for clamping the respective duplicate sections, which are aligned to a sensor such as a scanner. Traditionally, the duplicate section is then taken up into a so-called holding cup, which may contain a silicone mass, in which the duplicate section to be measured is fixable.

For referencing it is particularly planned that the duplicate is mounted on a reference containing base plate, which is split apart, for example by sawing. The individual base plate sections thereby exhibit the required references to ensure a geometric or spatial allocation of the duplicate sections, which have to be scanned separately.

It is thereby especially provided, that the duplicate is surface-ground on the underside, to then be attached to the base plate exhibiting a surface-ground surface.

The invention is characterized in particular by the procedural steps consisting of:
  Taking a casting of at least one of the residual tooth areas comprising part of the jaw;
  Fabrication of the duplicate preferably by filling the casting with plaster;
  Mounting of the duplicate on the base plate having the references (dental model);
  Splitting of the dental model for gaining model sections which comprise the duplicate sections;
  Measuring of the duplicate sections for capturing the form data and the references provided on the respective base plate sections;
  Match up of data corresponding to the references of the individual model sections, with the reference data stored in the computer; and
  Fabrication of the dental restoration under consideration of the form data and the data gained by matching.

In other words, by capturing the reference data with the data gained from the references provided on the individual model sections, the spatial allocation of the duplicate sections is determined. These data are then linked with the form data; that is data corresponding to the forms of the individual duplicate sections, in order to be able to fabricate the dental restoration, as is for example disclosed in principle in WO 99/47065 or WO 03/007834.

It is especially provided that geometrical properties of the base plate and/or markings are used as references. Possible markings may be points or lines on the base plate. Geometric properties to be mentioned preferably are delimitations such as edges or surfaces of the base plate.

In particular, inner and/or outer longitudinal side walls of the base plate should consist of a zigzag- or wave-shaped geometry, whereby the corresponding geometry is selected such that an unequivocal allocation of base plate sections to each other is ensured. Thus, in a zigzag geometry the height of the elevation or the distance thereof, may be varied to the extent required. The same applies for wave-shaped geometry.

In a zigzag geometry, the respective peaks may also be used as reference points, even if these get damaged for example, in as far as the delimiting surfaces of the base plate cutting the peaks also exhibit an unequivocal geometric position to each other, whereby a referencing takes place.

To ensure that the duplicate to be mounted onto the base plate does not cover the references provided on the base plate, the duplicate has to be spaced to the inner and outer edge of the base plate.

A referencing may, however, also take place directly after taking the casting. Thus, an impression spoon may for example be realized, such that references are obtained in the casting. Other analogous measures are possible as well. References may also be applied directly to the casting.

Further details, advantages, and features of the invention not merely derive from the patent claims—by themselves and/or in combination—but also from the following description of a preferred embodiment which is revealed through the drawing.

Shown are:

FIG. 1 a basic diagram of a duplicate;

FIG. 2 a base plate holding the duplicate according to FIG. 1;

FIG. 3 a dental model consisting of a duplicate according to FIG. 1, and a base plate according to FIG. 2;

FIG. 4 a form for the holding sections of the dental model in a correct position according to FIG. 3; and FIG. 5 a basic diagram of a holding device holding a section of the dental model according to FIG. 3 with a thereto aligned sensor.

In FIG. 1 a positive model designated as duplicate 10 is depicted in a situation within the mouth of the patient. Duplicate 10 therefore corresponds to a residual tooth area which is to be fitted with a dental restoration such as bridge or framework. Herefore, a casting is produced in the traditional way starting from a dental preparation of at least the affected tooth to be fitted with the restoration, corresponding to the negative model of the situation in the mouth of the patient. Hereby, the negative model is to represent not only the affected tooth, but also the adjacent teeth or their aproximal surfaces. A positive model is produced from the casting or the impression, which typically consists of plaster. The duplicate 10 may have reference marks 17 thereon.

Then the duplicate 10 is surface-ground on the underside (surface 12) to be attached (e.g., glued) to a plane surface 14 of a ready-made base plate 16. Hereby, the base plate exhibits the geometry of an arc shape that corresponds to the jaw. If needed, several sizes of base plates 16 may be provided to facilitate adjustment of individual duplicates.

Independent from this, the base plate 16 exhibits reference marks 17a, which make or form a referencing. The references may in particular be predetermined by a special realization of the base plate 16. Thus, the embodiment provides for a specially formed geometric shape of the outer sidewall 18, or the inner sidewall 20, or their surfaces, which form references. Thereby the surfaces 18, 20 are shaped such that each section of the base plate 16 is referenced individually, that is, is designated, with the consequence, that taking into consideration the respective reference an unmistakable geometrical or spatial allocation of the respective sections of the base plate 16 to each other is ensured. By attaching the duplicate 10 onto the surface 14 of the base plate 16 the sections of the duplicate 10 consequently also exhibit an unequivocal spatial allocation to each other. The base plate attached to the duplicate 10 is shown in FIG. 3. The unit formed this way may be designated as dental model 21.

After attaching the duplicate 10 on the base plate 16, model sections 24 are cut out from the duplicate 10 together with the base plate 16, which correspond to individual teeth, toothless jaw sections, or roots which are to be fitted with the dental restoration or determine their realization. The model sections 24 of the dental model 21 therefore consist of a duplicate section 26, as well as a section 28 of the base plate 16.

The model section 24 to be measured in each case is placed into a holding device 30 in order to capture the geometry by means of a sensor 32 such as a scanner, and to feed the respective measuring values as digital data into the computer, in which the data corresponding to the referencing are stored. Thus, the only thing to be done is to match up the data of the model sections 24 in relation to the reference geometry stored in the computer, and thereby match them to each other to obtain a data record. In other words, the data corresponding to the referencing are matched to the data gained from the references of the model sections, to achieve a spatial allocation of the duplicate sections which corresponds to the situation in the mouth of the patient. In addition to the position data of the respective model section, form data of the respective duplicate section attached on the model section are also available. The dental restoration is then automatically produced from these data as is revealed in principle in WO 99/47065 or WO 03/007834. Hereby, express reference is made to these disclosures.

In the embodiment the holding device 30 is realized as cup 34 which contains a holding mass such as silicone rubber 36 for holding and fixing the base plate section 28 and therefore the model section 24. The cup 34 may then be rotated around its longitudinal axis 38, as symbolized by the arrows 40, 42. Hereby, an alignment to the sensor 32 takes place to the desired degree, to be able to capture or scan the model section 24 to the required degree. Thereby the referencing, i.e. the reference points of the base plate section 28 are captured so that an unequivocal geometrical allocation of the respectively captured duplicate section 26 to the total duplicate 10, or the position of duplicate section 26 in duplicate 10 can be determined.

Obviously there is also the option to additionally move the model section 24 consisting of the base plate section 28 and the duplicate section 26 along the X and Y direction of a rectangular system of coordinates to capture the geometry.

In other words, a relative movement by desired degrees of freedom may take place between the model section 24 and the sensor 32. If needed, the sensor 32 may also be aligned to section 24 to the extent required.

In order to align the model sections in the correct position when fitting the fabricated restoration, a form 22 may be used, as is e.g. known from the "Model-Tray" system (FIG. 4).

Pursuant to the invention a geometrical determination of the model of a jaw section to be fitted with a dental prosthesis is available by means of simple process.

The invention claimed is:

1. In a process for determining the form of a duplicate of a residual tooth area which is to be fitted with a dental restoration, in which duplicate sections to be fitted with the dental restoration and/or duplicate sections determining dental restoration geometry are removed from the duplicate and form data to be allocated to the forms of the duplicate sections is determined and stored in a computer, by means of which the form of the dental restoration is calculated taking into consideration the spatial allocation of the duplicate sections, the improvement comprising storing in a computer a referencing of a base plate for the duplicate or a referencing on the duplicate produced during fabrication of the duplicate, separately placing sections of the duplicate or sections of the duplicate together with corresponding sections of the base plate connected thereto in a holding device and determining with a sensor, geometry of each duplicate or duplicate/base plate section, individually referencing the duplicate sections as to spatial allocation to each other in the referencing stored in the computer, and which is independent of the duplicate, and comparing the referencing stored in the computer with the separately determined duplicate or duplicate/base plate sections to determine the form of the duplicate of the residual tooth area.

2. Process according to claim 1, comprising the steps of:

taking a casting of at least one of the residual tooth areas comprising part of the jaw;

fabricating the duplicate by filling the casting with plaster;

mounting the duplicate on the base plate, where the base plate or the duplicate has references thereon which is stored in the computer;

splitting the base plate with the duplicate mounted thereon to obtain the duplicate/base plate sections;

performing said separately placing step, followed by said determining step, thereby measuring the duplicate/base plate sections for capturing form data and the references provided on the respective base plate sections or the duplicate sections;

performing said individually referencing step, thereby matching up data, which correspond to the references of the base plate sections or the duplicate sections, with the referencing data stored in the computer; and fabricating a dental restoration under consideration of the form data and the data gained by said matching.

3. Process according to claim 2, wherein the duplicate is directly provided with the references.

4. Process according to claim 3, wherein the references are produced when making the casting.

5. Process for determining the form of a duplicate of a residual tooth area which is to be fitted with a dental restoration, comprising the steps of:

taking a casting from at least one residual teeth area of a jaw to be fitted with a dental restoration, fabricating a model from the casting as the duplicate by filling the casting with plaster, attaching the duplicate to a base plate, where the duplicate or the base plate has references thereon, splitting the base plate with the duplicate attached thereto apart to obtain duplicate/base plate sections, measuring the duplicate/base plate sections taking into consideration the references from the base plate sections, onto which the duplicate sections are arranged, or the references from the duplicate sections, storing in a computer a referencing of the base plate for the duplicate or a referencing on the duplicate produced during fabrication of the duplicate, which is independent of the duplicate and individually referencing the duplicate/base plate sections as to spatial allocation to each other in the referencing stored in the computer, and which is independent of the duplicate.

6. Process according to claim 5, wherein geometrical properties of the base plate and/or markings are used as the references.

7. Process according to claim 6, wherein the base plate contains points and/or lines as the markings.

8. Process according to claim 6, wherein the base plate contains geometrical properties delimitations in the form of edges or surface sections.

9. Process according to claim 5, additionally comprising surface grinding the duplicate on an underside and attaching the underside to a planar surface of the base plate following a tooth arc.

10. Process according to claim 9, wherein the duplicate is attached to the base plate such that the duplicate is spaced on all sides from an edge of the base plate.

11. Process according to claim 5, wherein the base plate exhibits along a longitudinal wall running along the duplicate, a texture.

12. Process according to claim 11, wherein the texture is a wave-shaped and/or zigzag geometry.

13. Process according to claim 12, wherein intersections or virtual interfaces of peripheries of the wave-shaped and/or zigzag geometry are used as the references.

14. Process according to claim 5, wherein references are applied directly to the casting.

* * * * *